US010702411B2

(12) United States Patent
Song et al.

(10) Patent No.: US 10,702,411 B2
(45) Date of Patent: Jul. 7, 2020

(54) VARUS/VALGUS CORRECTING DEVICE (71) Applicants: Dong Ho Song, Seoul (KR); Jinwook Song, Daegu (KR)

(72) Inventors: Dong Ho Song, Seoul (KR); Jinwook Song, Daegu (KR); Joon Han Kang, Seoul (KR)

(73) Assignees: Dong Ho Song, Seoul (KR); Jinwook Song, Daegu (KR)

( * ) Notice: Subject to any disclaimer, the term of this patent is extended or adjusted under 35 U.S.C. 154(b) by 0 days.

(21) Appl. No.: 16/322,517

(22) PCT Filed: Apr. 6, 2018

(86) PCT No.: PCT/KR2018/004092
§ 371 (c)(1),
(2) Date: Feb. 1, 2019

(87) PCT Pub. No.: WO2018/190580
PCT Pub. Date: Oct. 18, 2018

(65) Prior Publication Data
US 2019/0358073 A1    Nov. 28, 2019

(30) Foreign Application Priority Data
Apr. 14, 2017    (KR) .................. 10-2017-0048294

(51) Int. Cl.
*A61F 5/01*    (2006.01)
(52) U.S. Cl.
CPC .......... *A61F 5/0123* (2013.01); *A61F 5/0127* (2013.01); *A61F 2005/0165* (2013.01); *A61F 2005/0179* (2013.01)

(58) Field of Classification Search
CPC ........ A61F 5/01; A61F 5/0102; A61F 5/0123; A61F 5/0127
USPC .................... 602/16, 23, 27, 29, 24–26
See application file for complete search history.

(56) References Cited

U.S. PATENT DOCUMENTS

| 5,486,157 A | * | 1/1996 | DiBenedetto | ......... A61F 5/0127 |
| | | | | 602/16 |
| 7,112,181 B1 | * | 9/2006 | DeToro | ................. A61F 5/0127 |
| | | | | 602/27 |
| 8,814,815 B2 | | 8/2014 | DeHeer | |
| 8,882,688 B1 | * | 11/2014 | Ancinec | ............... A61F 5/0125 |
| | | | | 128/882 |
| 8,968,228 B2 | | 3/2015 | Graddon et al. | |

(Continued)

FOREIGN PATENT DOCUMENTS

| CN | 2031660 U | 2/1989 |
| CN | 102711678 A | 10/2012 |

(Continued)

OTHER PUBLICATIONS

International Search Report of PCT/KR2018/004092, dated Jul. 16, 2018, English translation.

(Continued)

*Primary Examiner* — Keri J Nelson
(74) *Attorney, Agent, or Firm* — STIP Law Group, LLC (57) ABSTRACT The present disclosure relates to a varus/valgus correcting device, and more particularly, to a varus/valgus correcting device devised to correct varus (i.e., genu verum (O-shaped leg)) and valgus (i.e., genu valgum (X-shaped leg)) by rotating tibia and fibula and allow a wearer to easily walk.

10 Claims, 8 Drawing Sheets

(56) References Cited

U.S. PATENT DOCUMENTS

2012/0010548 A1    1/2012  Scholtes
2012/0283613 A1  11/2012  DeHeer et al.
2013/0165833 A1*  6/2013  Blanck .................. A61F 5/0127
                                                                602/27
2016/0058595 A1    3/2016  Tsitouras

FOREIGN PATENT DOCUMENTS

KR        100309930 B1    9/2001
KR      1020130083299 A    7/2013
KR        101352480 B1    1/2014

OTHER PUBLICATIONS

Office Action from China National Intellectual Property Administration of 201880002975.4, dated Aug. 12, 2018.
Office Action from Japan Patent Office of 2019-507909, dated Sep. 17, 2019.

* cited by examiner

VARUS/VALGUS CORRECTING DEVICE

CROSS-REFERENCE TO RELATED APPLICATIONS

This application is the U.S. National Phase under 35 U.S.C. § 371 of International Application No. PCT/KR2018/004092 filed on Apr. 6, 2018, which in turn claims the benefit of Korean Application No. KR10-2017-0048294, filed on Apr. 14, 2017, the disclosures of which are incorporated by reference into the present application.

BACKGROUND OF THE INVENTION

Field of the Invention

The present disclosure relates to a varus/valgus correcting device, and more particularly, to a varus/valgus correcting device devised to correct varus (i.e., genu verum (O-shaped leg)) and valgus (i.e., genu valgum (X-shaped leg)) by rotating tibia and fibula and allow a wearer to easily walk.

Related Art

The varus/valgus correcting device is an apparatus for correcting varum (O-shaped leg) and valgus (X-shaped leg) due to deformity of a knee joint. The knee joint is a joint located between bones of three parts of a lower end of the femur, an upper end of the tibia, and a rear side of the kneecap. Inward or outward bowing of the leg due to deformity at the knee joint due to various causes such as rickets, osteomalacia, cartilage growth disorder, endocrine disorder, sway posture, unbalanced diet, nutritional imbalance, lack of exercise, and the like, is referred to as angular deformity, and the angular deformity includes varus and valgus.

The knee flexion is a knee flexion of the knee in the knee, and the angle between the anatomical axis of the femur and the anatomical axis of the tibia is 180 degrees or more. When the two legs are gathered together, the knee is not attached to each other, but has an O shape bent outward. It is often called an inner leg or an O-shaped leg, and the inner leg is bilateral due to an inverted leg which is the opposite to the outer leg.

Outward bowing of the knee at the knee joint is termed genu varum, and an angle formed when an anatomical axis of the thigh and an anatomical axis of the tibia meet is 180° or greater. The genu varum has an appearance in which the knees are not touched but bent outward in an O-shape when standing on two legs, which is generally called bow-legs or O-shaped legs. Varus is a bilateral lower limb deformity which is the opposite of the valgus.

The varus in which a distance between knee joints spacing at the knees is 5 cm or greater when ankles are in contact is considered a serious deformity and reported as a target of a surgical treatment.

Bow legs make leg lines look bad and cause gait disorders, chronic fatigue, spinal deformity, aging, back pain, and neuralgia. In addition, deformation of the legs are aggravated over time, accelerating the overall structural deformation including the spine and the pelvis, promoting aging and causing secondary problems such as arthritis and back pain discs. Common symptoms of those with bow legs are that they feel fatigue easily and may not walk for a long time, and sometimes, they complain of the pain of both knee joints.

Meanwhile, valgus (or knock-knees) refers to a condition in which lower limbs are bowed outwards at the knee joints, i.e., the knees are bowed, and the bowed shape of the lower limbs is similar to the alphabet X, and thus, it is called X-shaped legs. An appearance in which an angle where an anatomical axis of the thigh and an anatomical axis of the tibia meet is smaller than 165° is regarded as valgus. As a method for easily diagnosing knock-knees, the knock-knees are suspected when a space between ankles is 2 to 3 centimeters or greater when the legs are straightened.

Symptoms such as the bow-legs or the knock-knees, that is, the legs are bowed result from a bad posture such as a wrong walking habit, a foot posture often supported by one foot, sitting with one's legs crossed, and the like. If the wrong posture is maintained, muscle balance or balance of flexibility is lost to cause distortion at a hip joint, a knee joint, an ankle joint, and the like.

In addition, shortage of vitamin D that forms the bone causes the bow legs. Vitamin D is formed when the body is exposed to sunlight. In the case of adolescents, they often go to school early in the morning and leave school late at night, which may lead to insufficient opportunities for the production of vitamin D, which weakens health of the bones, causing bow legs. It is also known that varus (O-shaped legs) and valgus (X-shaped legs) legs are hereditary.

Neglecting the bow-legs or the knock-knees may cause a secondary disease, which may adversely affect health. Diseases that may occur when the legs are bowed may be classified as athletic system diseases, medical diseases, and psychiatric diseases.

First, the diseases of the athletic system diseases include arthritis, degenerative joint deformity, plantar area pain, palmoplantar keratoderma, and overtoe due to unbalance of body transfer due to imbalance of a body musculoskeletal structure such as internal curve of lower limbs, loss of lumbar curvature, and the like. Individuals who suffer such diseases commonly get easily tired and deteriorate in physical strength.

In addition, bow-legs cause the chain of change in a body structure, and thus, back pain, disc, sciatica, shoulder pain, shoulder discomfort, and the like, may occur.

Next, medical diseases that may occur due to varus and valgus include a digestive trouble, gastritis, gastroptosis, cold hypersensitivity of lower abdomen, menstrual cramps, menstrual irregularities, heart disease, lung diseases, skin diseases, headache, and stroke. Especially, a difference in length between both legs causes complications. When the left leg is long, it is likely to cause diseases of genitourinary or digestive system, and when the right leg is long, it may cause a heart disease, a respiratory disease, a skin ailment, and the like. Finally, the psychiatric diseases include loss of self-esteem, low sprits, and depression in severe cases.

As described above, untreated varus and valgus may cause a secondary disease to adversely affect health, and thus, varus and valgus needs to be treated through correction. Most varus and valgus (referred to as "varus/valgus") result from internal or external rotation deformity of bones or joints, and thus, the rotationally deformed bones or joints may be reversely rotated and corrected to the original state to straighten the array of bones, thus normally recovering the legs.

As the related art related to an apparatus for correcting varus and valgus by reversely rotating the bones or joints, Korean Patent Registration No. 10-1352480 (Jan. 17, 2014) relates to a leg correcting device, which, specifically, discloses a technique related to a leg correcting device capable of fixing most appropriate portions at appropriate positions along a length direction of bowed legs and simultaneously rotating tibia and fibula to provide an effect of correction to both varus and valgus caused as the splint bones themselves are bowed or as two knee joints are bowed outward. Also, Korean Patent Registration No. 10-0309930 (Nov. 1, 2001) relates to a tibia and fibula reverse-rotation correcting device, which, specifically, discloses a technique related to a tibia and fibula (leg) reverse-rotation correcting device in which a leg straightener is attached to an upper portion and a central portion on the basis of a support fixture, shoes for correcting the feet are attached to a lower portion, and the femur and the hip joints are prevented from rotating during straightening.

The technical configurations described in Korean Patent Registration Nos. 10-1352480 and No. 10-0309930 both related to techniques regarding a varus/valgus correcting device including a leg support part supporting legs, a leg fixing part fixing the legs, and a foot fixing part fixing feet. However, the both techniques have a problem in that a user who wears the correcting devices cannot stably set foot on the bottom due to a structural problem of the part for fixing the feet and cannot smoothly bend the ankles, and thus, there is a problem of wearing the correcting device and walking thereon.

Meanwhile, U.S. Pat. No. 8,968,228 B2 (Mar. 3, 2015) and U.S. Pat. No. 8,814,815 B2 (Aug. 26, 2014), and U.S. Patent Laid-Open Publication No. 2016-0058595 A1 (Mar. 3, 2016) disclose techniques related to leg correcting device including a part for fixing legs and feet and bent at an ankle part. However, like the technique mentioned above, these techniques also do not include a technique of adjusting a horizontal angle of the part for fixing legs and a related component, and thus, are not possible to reversely rotate the bones or joints to correct varus and valgus.

SUMMARY

An aspect of the present disclosure provides a correcting device which corrects varus (O-shaped legs) and valgus (X-shaped legs), allows the ankle to be smoothly bent and stretched when a user who wears the correcting device walks, and allows the wearer to stably step on the floor (or ground).

Another aspect of the present disclosure provides a varus/valgus correcting device which is independently bent and stretchable at a knee position and an ankle position to allow a user who wears the correcting device to easily bend a knee part and an ankle part when the wearer walks or is relaxed.

Another aspect of the present disclosure provides a varus/valgus correcting device capable of correcting varus (O-shaped legs) and valgus (X-shaped legs) by rotating tibia and fibula through a method of adjusting a horizontal angle of a corrective shoe (or orthopedic shoe) for fixing a foot.

According to an aspect of the present disclosure, there is provided a varus/valgus correcting device including: a support frame provided with a leg fixing part and a corrective shoe, supporting at least one of upper and lower limbs of a leg, and formed in a vertical length direction of the leg; at least one leg fixing part selected from among a femoral fixing part connected to the support frame and installed to surround and fix the upper limb of the leg, a knee fixing part connected to the support frame and installed to fix a knee part, and a calf fixing part connected to the support frame and installed to surround and fix the lower limb of the leg; and a corrective shoe connected to a lower portion of the support frame and installed to fix a foot, wherein a connection portion of the support frame connected to the corrective shoe is positioned between a bottom of the corrective shoe and a highest level of the corrective shoe.

The corrective shoe may be horizontally rotated to be adjusted in correction angle to correct varus/valgus.

The connection portion of the support frame connected to the corrective shoe may be positioned on a rear side, a lateral side, or a combination thereof of the corrective shoe.

The support frame may include: an upper support frame supporting an upper limb of the leg; and a lower support frame supporting a lower limb of the leg, and the upper support frame, the lower support frame, and a coupling portion thereof may include a knee bending part having a structure bent according to a bending angle of a knee.

A corrective shoe support part connecting the corrective shoe to the support frame in a horizontal direction may be provided between the support frame and the corrective shoe, so that the corrective shoe and the support frame are connected to each other and the corrective shoe support part may be positioned between the bottom of the corrective shoe and the highest level of the corrective shoe.

A correction angle adjusting part may be installed on the corrective shoe support part or the support frame coupled to the corrective shoe support part and adjust a horizontal angle of the corrective shoe support part to adjust a correction angle of the corrective shoe.

The correction angle adjusting part may include a correction angle display part displaying a correction angle of the corrective shoe.

The upper support frame or the lower support frame may each be provided as a single shaft on the rear of the leg or may be provided as a pair of shafts inside or outside the leg.

The knee bending part may be maintained in a straightened state when an external force is not applied by an elastic member including at least one selected from among a spring, a wire, and rubber.

The femoral fixing part and the calf fixing part, when installed at the support frame, may be adjustable in height in a length direction of the leg, or the support frame may be adjustable in length in a vertical length direction of the leg.

The leg fixing part may include: a leg horizontal support part supporting the side of the leg such that the leg is not rotated together according to a change in correction angle of the shoe; and a leg fixing belt allowing the leg horizontal support part to surround and fix the leg according to a thickness of the leg.

The corrective shoe support part may further include: an ankle bending part configured to be bent or stretched according to a vertical movement of an ankle.

The varus/valgus correcting device may further include: a femur correcting part connected to the support frame, surrounding and fixing the upper limb of the leg, and rotating in an inward direction or outward direction of the leg to correct a femur in the inward direction or outward direction of the leg, and here, the varus/valgus correcting device may further include a femur rotation angle adjusting part adjusting a rotation angle of the femur in an inward or outward direction of the leg.

When the varus/valgus correcting device further includes the femur correcting part, the varus/valgus correcting device may allow the femoral fixing part to additionally include a function of rotating in the inward direction or outward direction of the leg to additionally serve as the femur correcting part.

According to the varus/valgus correcting device, since the connection portion of the support frame connected to the corrective shoe is positioned between the bottom of the corrective shoe and the highest level of the shoe, when the user wearing the correcting device walks, the ankle may be smoothly bent or stretched, providing ease in movement, and the user may stably step on the floor when moving.

In addition, according to the varus/valgus correcting device, since the knee position and the ankle position may be independently bent or stretched, when the user wearing the varus/valgus correcting device walks or is relaxed, the knee part and the ankle part may be easily bent. Thus, since mobility is applied to the knee and ankle joints, the effect of correction may be further maximized.

BRIEF DESCRIPTION OF THE DRAWINGS

The embodiments will be described in detail with reference to the following drawings in which like reference numerals refer to like elements wherein:

FIGS. 2(a), (b), (c), (d), (e) and (f) are view illustrating configurations of various examples of a varus/valgus correcting device according to an embodiment of the present disclosure.

FIGS. 3(a) and (b) are a view illustrating a corrective shoe and a correction angle adjusting part of a varus/valgus correcting device according to an embodiment of the present disclosure.

FIGS. 4(a), (b), (c) and (d) are a view illustrating position adjustment of a leg fixing part in a varus/valgus correcting device according to the embodiment of the present disclosure.

FIGS. 5(a) and (b) are a view illustrating a configuration of a varus/valgus correcting device according to another embodiment of the present disclosure.

FIGS. 6(a), (b), (c), (d), (e) and (f) are a view illustrating configurations of various examples of a varus/valgus correcting device according to another embodiment of the present disclosure.

FIGS. 8(a) and (b) are a view illustrating a femur correcting part of a varus/valgus correcting device according to an embodiment of the present disclosure.

DETAILED DESCRIPTION

Throughout the accompanying drawings, the same reference numerals are used to designate the same or similar components, and redundant descriptions thereof are omitted. Further, in the following description, the terms "first," "second," "one side," "the other side" and the like are used to differentiate a certain component from other components, but the configuration of such components should not be construed to be limited by the terms.

In the following description, when a detailed description of the relevant known function or configuration is determined to unnecessarily obscure the gist of the present invention, the detailed description will be omitted.

The embodiment described in the present disclosure and the configuration illustrated in the drawings are merely the most preferred embodiment of the present invention, rather than representing all the technical concepts of the present invention, so the present invention is meant to cover all modifications, similarities and alternatives which are included in the spirit and scope of the present invention at the time of filing of the present invention.

Hereinafter, embodiments of a varus/valgus correcting device 100 according to the present disclosure will be described with reference to the accompanying drawing such that a person skilled in the art to which the present invention pertains may easily realize the present invention.

Figure 1:
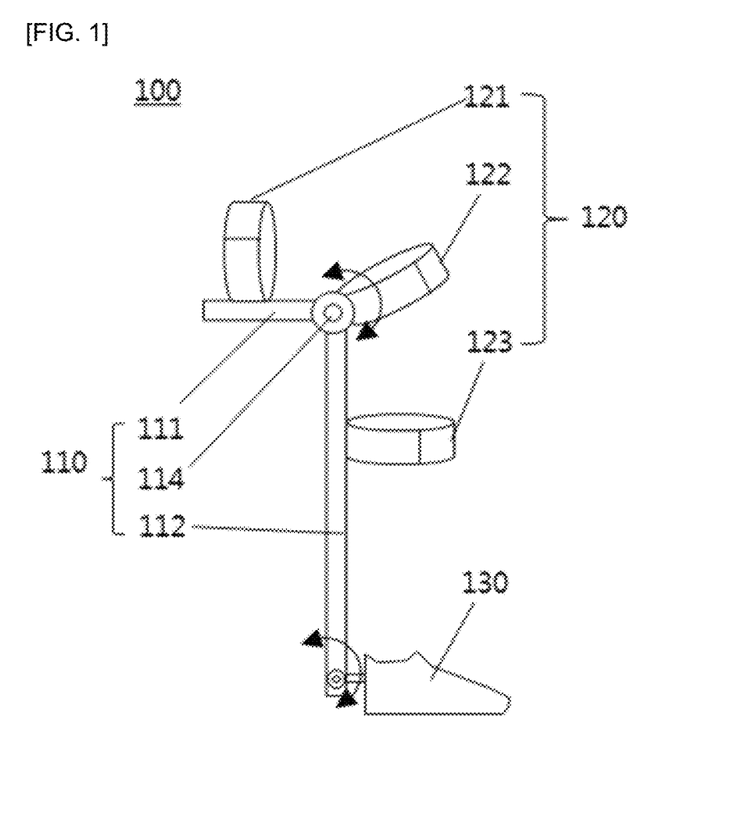
FIG. 1 is a view illustrating a configuration of a varus/valgus correcting device according to an embodiment of the present disclosure.
Figure 2:
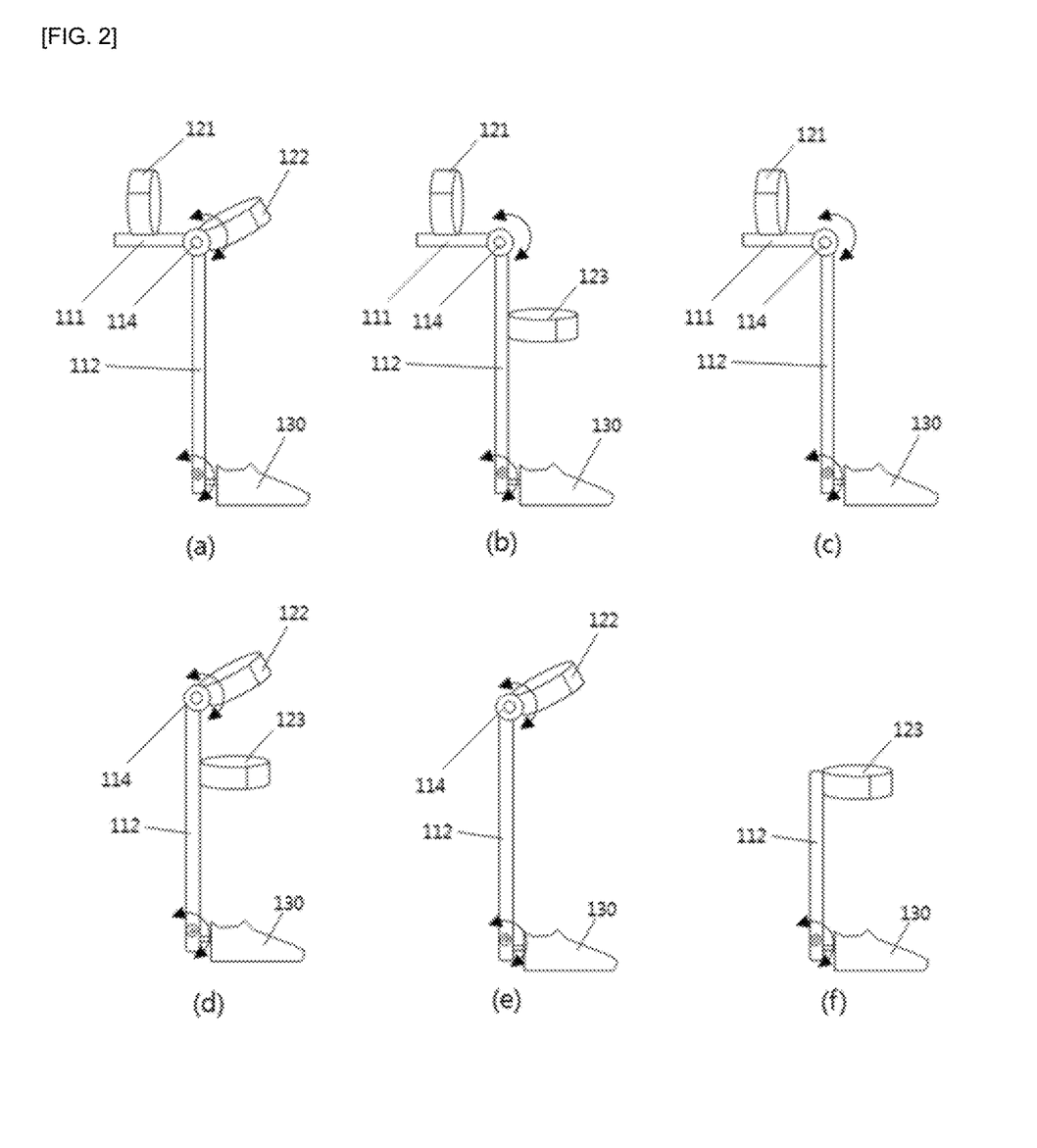

FIG. 1 is a view illustrating a configuration of a varus/valgus correcting device 100 according to an embodiment of the present disclosure, and FIG. 2 is a view illustrating configurations of various examples of a varus/valgus correcting device according to an embodiment of the present disclosure.

As illustrated in FIGS. 1 and 2, the varus/valgus correcting device 100 according to an embodiment of the present disclosure includes a support frame 110, a leg fixing part 120, and a corrective shoe 130.

The support frame 110 may be provided with the leg fixing part 120 and the corrective shoe 130, may support at least one of upper and lower limbs of a leg or the both, and is formed in a vertical length direction of the leg.

Meanwhile, the "upper limb of the leg" used in the present disclosure refers to part between a hip joint and the knees in the leg, and the "lower limb of the leg" refers to part between the knee and the ankle. In the present disclosure, the support frame 110 may include an upper support frame 111 supporting the upper limb of the leg and a support frame 112 supporting the lower limb of the leg. The upper support frame 111 and the lower support frame 112 may be integrally configured or detachably configured.

A knee bending part 114 having a structure that can be bent according to a bending angle of the knee is provided on the upper support frame 111, the lower support frame 112, or a coupling portion thereof, so that a user who wears the varus/valgus correcting device 100 according to the present disclosure may easily bend or straighten the knee.

That is, the knee bending part 114 is provided at a lower end portion of the upper support frame 111 or at an upper end of the lower support frame 112 or provided to be positioned at the coupling portion between the upper support frame 111 and the lower support frame 112. In FIGS. 1 and 2, it is illustrated that the knee bending part 114 is provided to be positioned between the upper support frame 111 and the lower support frame 112, for example.

For example, although the knee bending part 114 is located at the lower end portion of the upper support frame 111 or the upper end portion of the lower support frame 112, since the upper support frame 111 and the lower support frame 112 have the coupling portion therebetween, the upper support frame 111 and the lower support frame 112 may be connected to each other.

Meanwhile, the knee bending part 114 is maintained in a straightened state when an external force is not applied by an elastic member including at least one selected from among a spring, a wire, and rubber, to help the user who wears the varus/valgus correcting device 100 of the present disclosure walk.

That is, at an initial state of the varus/valgus correcting device 100 in which the user does not apply any force to the varus/valgus correcting device 100, the knee bending part is maintained in a straightened state, without being bent, to allow the user to easily wear the varus/valgus correcting device 100, and does not apply an unnecessary force when the user is standing.

Meanwhile, in the present disclosure, the initial state may be maintained at a predetermined angle in a state in which no force is applied to the varus/valgus correcting device 100 from the outside, so that the user may easily wear the varus/valgus correcting device 100 in a state in which the user is sit, while a bent state is maintained.

Meanwhile, in the present disclosure, the leg fixing part 120 may be connected to the support frame 110.

The leg fixing part 120 may include a femoral fixing part 121, a knee fixing part 122, and a calf fixing part 123 according to the fixed parts. The varus/valgus correcting device 100 according to the present disclosure may selectively include at least one of the femoral fixing part 121, the knee fixing part 122, and the calf fixing part 123.

A specific configuration and function of each of the leg fixing part 120 will be described in detail. The femoral fixing part 121 is connected to the support frame 110 to surround and fix the upper limb of the leg on the upper part of the knee, the calf fixing part 123 is connected to the support frame 110 to surround and fix the lower limb of the leg on the lower part of the knee, and the knee fixing part 122 is connected to the support frame 110 to fix the knee part. Here, the knee fixing part may be installed to accurately correspond to the knee position, but in case where the femoral fixing part or the calf fixing part is provided, the femoral fixing part or the calf fixing part may be provided at a position between a lower part of the femoral fixing part and the knee or at a position between the calf fixing part and the knee.

In the meantime, when the support frame 110 according to the present disclosure includes the upper support frame 111 and the lower support frame 112, the femoral fixing part 121 may be connected to the upper support frame 111 and the calf fixing part 123 may be connected to the lower support frame 112.

As described above, the knee fixing part 122 may be provided at a position between the lower part of the femoral fixing part and the knee or at a position between the calf fixing part and the knee. In this case, the knee fixing part 122 may be connected to the upper support frame 111 or the lower support frame 112, and when the knee fixing part 122 corresponds to a knee position, the knee fixing part 122 may be connected to the coupling portion between the upper support frame 111 and the lower support frame 112.

FIG. 2 illustrates various example configurations of a varus/valgus correcting device according to an embodiment of the present disclosure. Specifically, FIG. 2(a) shows a varus/valgus correcting device including the femoral fixing part 121, the knee fixing part 114, and the corrective shoe 130, FIG. 2(b) shows a varus/valgus correcting device including the femoral fixing part 121, the calf fixing part 123 and the corrective shoe 130, FIG. 2C shows a varus/valgus correcting device including the femoral fixing part 121 and the corrective shoe 130, FIG. 2(d) shows a varus/valgus correcting device including the knee fixing part 114, the calf fixing part 123, and the corrective shoe 130, FIG. 2(e) shows a varus/valgus correcting device including the knee fixing part 114 and the corrective shoe 130, and FIG. 2(f) shows a varus/valgus correcting device including the calf fixing part 123 and the corrective shoe 130. However, the varus/valgus correcting device according to the present disclosure is not limited to the configurations illustrated in FIG. 2.

Meanwhile, the varus/valgus correcting device 100 according to the present disclosure includes the corrective shoe 130 connected to a lower portion of the support frame 110 and installed to fix a foot. The corrective shoe maintains a shape of a general shoe, and a portion of an upper portion of the shoe may be opened to facilitate wearing the shoe or a string type or Velcro type fixing unit for fixing the shoe may be provided at an upper portion of the shoe for the sake of convenience.

In this case, a connection portion of the support frame 110 connected to the corrective shoe 130 is positioned between the bottom of the corrective shoe 130 and a highest level of the corrective shoe 130 so that the ankle of the user who wears the corrective shoe 130 may be freely bent and stretched in a vertical direction.

That is, in the case of the related art varus/valgus correcting device according to the related art, a foot fixing part for fixing the foot has an L-shaped bent portion, having a structural problem that an angle from the calf part to the sole through the ankle part cannot be changed, and thus, the user cannot stably step on the floor when the user wears the correcting device and walks. In addition, bending and stretching of the ankle are not smoothly made to cause the user to have a difficulty in walking in a state of wearing the correcting device. In contrast, in the present disclosure, since the connection portion of the support frame 110 connected to the corrective shoe 130 is positioned between the bottom of the corrective shoe 130 and the highest level of the corrective shoe 130, the support frame supporting the user from the calf part to the ankle part is not fixedly connected to the bottom side of the corrective shoe, thus solving the problem.

Here, the bottom of the corrective shoe refers to the lowermost surface of the shoe. If the bottom of the shoe is uneven, the bottom refers to the lowest portion. Also, the highest level of the shoe refers to a height up to the highest portion of the shoe when the shoe is generally placed on the bottom such that the user may wear it.

The 'connection portion' of the support frame connected to the corrective shoe may refer to a position of the support frame in contact with the corrective shoe when the corrective shoe is directly connected to the support frame by a fastening unit such as bolt-nut, or the like.

In this case, the connection portion of the support frame 110 connected to the corrective shoe 130 is located on a rear side, a lateral side, or a combination thereof of the corrective shoe 130, so that the user may stably step on the floor (or ground) when wearing the varus/valgus correcting device 100 and the corrective shoe 130 may be bent and stretched according to a vertical movement of the ankle when the user walks.

Meanwhile, in the present disclosure, the "connection portion" of the support frame connected to the corrective shoe may be connected to the corrective shoe through a connection with an additional component.

More specifically, a corrective shoe support part 140 connecting the corrective shoe to the support frame 110 in a horizontal direction (right angle direction with respect to a length direction of the support frame) is provided between the support frame 110 and the corrective shoe 13 in the varus/valgus correcting device 100, whereby the corrective shoe and the support frame may be connected and the corrective shoe support part may be positioned between the bottom of the corrective shoe and the highest level of the corrective shoe.

Also, as described above, in a case where the corrective shoe support part connecting the corrective shoe to the support frame in the horizontal direction is provided, the corrective shoe support part may be disposed on the rear side, the lateral side, or a combination thereof of the corrective shoe, and as described above, a separate ankle bending part 160 may be provided at a lower portion of the lower support frame or the corrective shoe support part.

In order to allow the corrective shoe 130 to be bent and stretched in accordance with a vertical movement of the ankle, the varus/valgus correcting device 100 according to the present disclosure may include the separate ankle bending part 160 at a lower portion of the lower support frame or at the corrective shoe support part.

Figure 3:
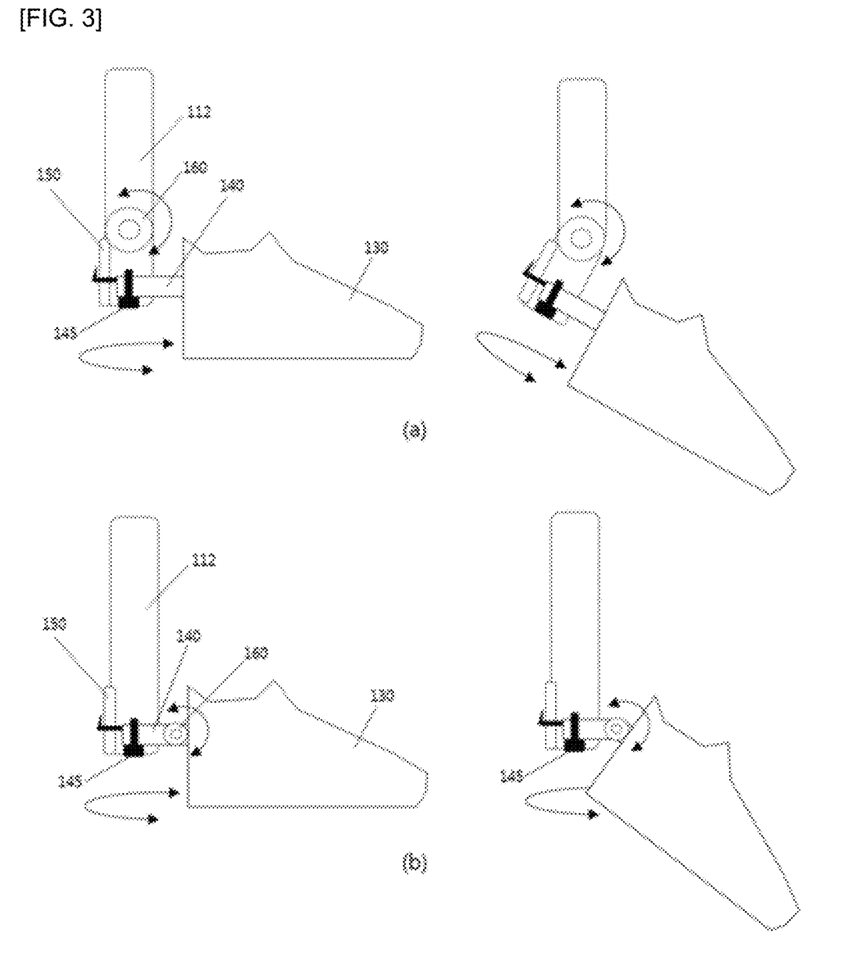

FIG. 3(*a*) is a view illustrating a bending operation of the ankle when the ankle bending part 160 is positioned at a lower portion of the lower support frame, and FIG. 3(*b*) is a view illustrating a bending operation of the ankle when the ankle bending part 160 is positioned at the corrective shoe support part 140.

As illustrated in FIG. 3(*a*), when the ankle bending part 160 is positioned at a lower portion of the lower support frame, the ankle bending part 160 may be installed at a lower portion of the lower support frame connected to the corrective shoe support part 140, and if it is not easy to position the ankle bending part at the lower position portion of the lower support frame connected to the corrective shoe support part due to the corrective angle support part 140, a correction angle display part 150, the ankle bending part 160 may be positioned at an upper portion than the lower position of the lower support frame connected to the corrective shoe support part 140.

Figure 4:
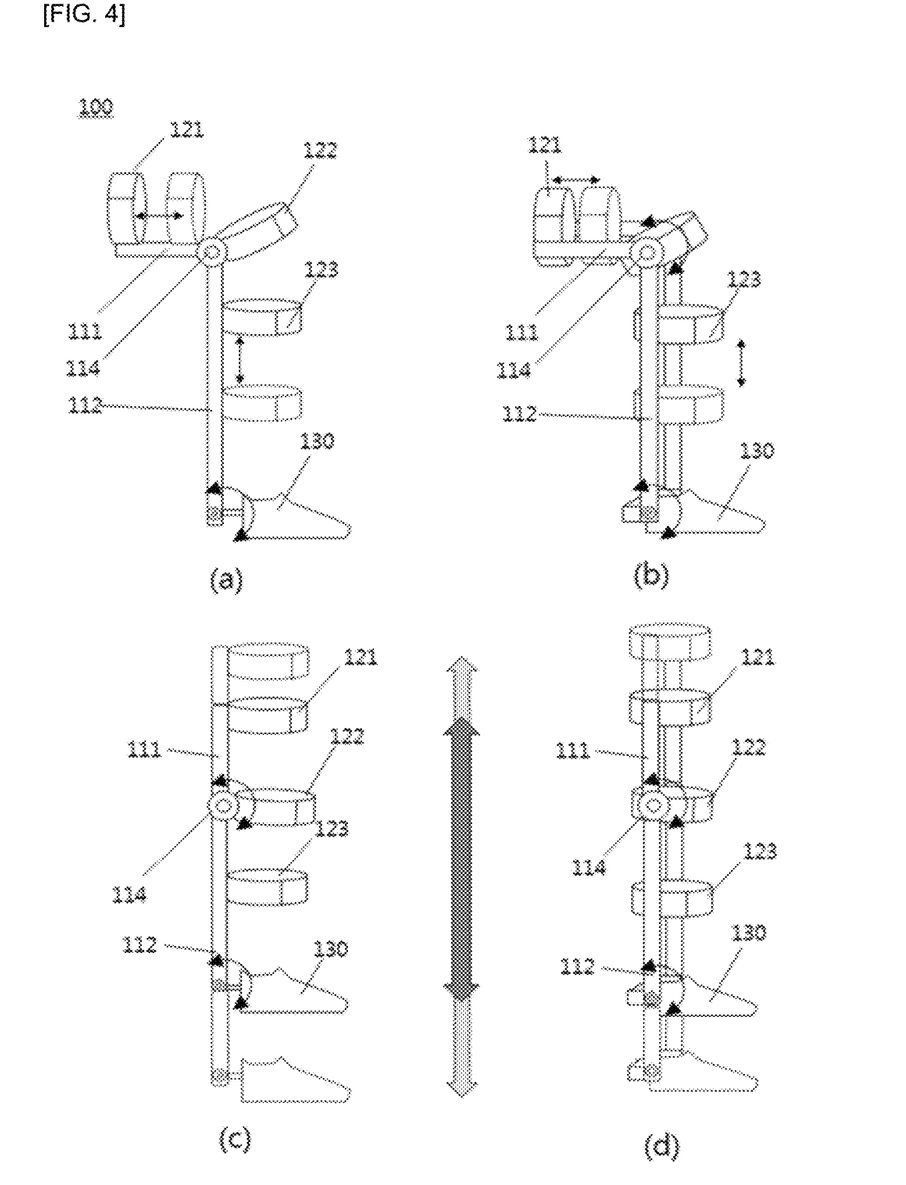

Meanwhile, the leg fixing part according to the present disclosure may be adjustable in height in a length direction of the leg. Referring to FIG. 4, FIGS. 4(*a*) and 4(*b*) illustrate position adjustment of the leg fixing part 120 in the varus/valgus correcting device 100 according to another embodiment of the present disclosure. When installed at the support frame 110, the femoral fixing part 121 and the calf fixing part 123 may be adjustable in height in the length direction of the leg so as to be worn according to lengths of various users.

Also, the support frame according to the present disclosure may be adjustable in length in the vertical direction of the leg. That is, as illustrated in FIGS. 4(*c*) and 4(*d*), each of the upper support frame and the lower support frame has a recess, which is adjustable in height, such as a plurality of coupling recesses in the support frame, and the length thereof may be adjusted by a bolt-nut, or the like. Also, a fastening portion which is adjusted in length using a screw rod and a nut or a toothed portion and a latch may be provided at the coupling portion of the upper support frame and the lower support frame, so that the user may simply adjust the length.

Also, the support frame according to the present disclosure may be configured as a single shaft or two shafts. Referring to FIGS. 1 to 6, the upper support frame or the lower support frame are configured as one shaft at the rear of the leg in FIGS. 1 and 2, and the upper support frame or the lower support frame are configured as a pair of shafts on an inner side and an outer side of the leg in FIGS. 5 and 6. However, the present disclosure is not limited thereto and may be variously applied.

Figure 5:
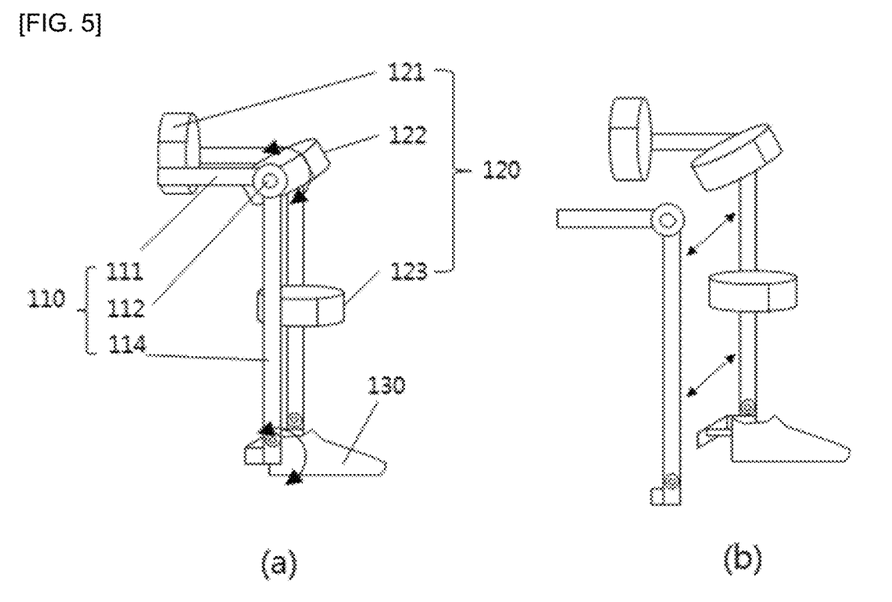
Figure 6:
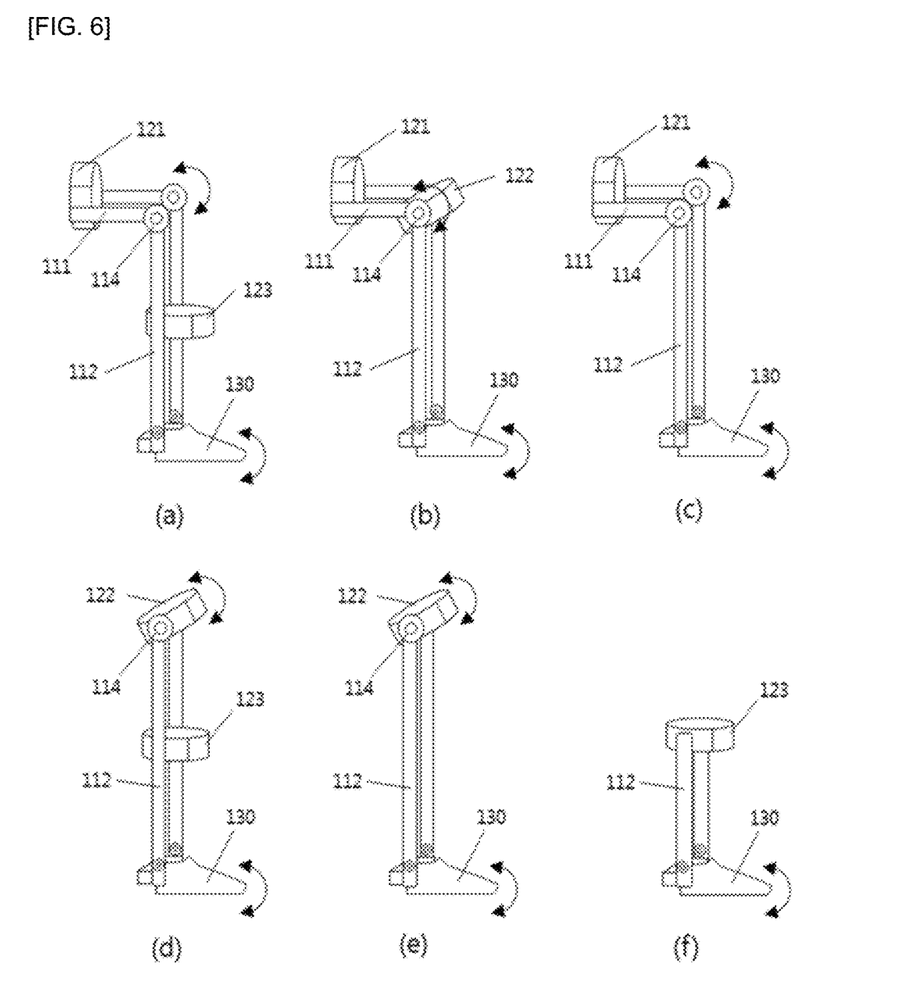

For reference, FIG. 5(*a*) is a view illustrating a varus/valgus correcting device of the present disclosure in which a support frame is provided as a pair of shafts inside and outside of the leg, and FIG. 5(*b*) is a view illustrating a varus/valgus correcting device in which one of a pair of support frames is separated to help understand the structure.

Also, FIG. 4(*a*) illustrates the upper support frame or the lower support frame provided as a shaft on the rear of the leg, and FIG. 4(*b*) illustrates the upper support frame or the lower support frame provided as a pair of shafts inside and outside the leg.

That is, both of the upper support frame 111 and the lower support frame 112 may be provided as a shaft at the rear of the leg or may be provided as a pair of shafts inside and outside the leg, the upper support frame 111 may be provided as a shaft at the rear of the leg, the lower support frame 112 may be configured as a pair of shafts inside and outside the leg, the upper support frame 111 may be configured as a pair of shafts inside and outside the leg, and the lower support frame 112 may be provided as a shaft at the rear of the leg.

In the present disclosure, at least one leg fixing part selected from among the femoral fixing part 121, the knee fixing part 122, or the calf fixing part 123 may include a leg horizontal support part supporting a side surface of the leg and a leg fixing belt.

Here, the leg horizontal support part supports the side surface of the leg so that the leg may not rotate together with the leg according to a change in a correction angle of the shoe. The leg horizontal support part extends in a vertical direction from the support frame 110 to surround the leg, and a material of the leg horizontal support part may include plastic or metal frame and a soft fiber material, rubber, silicon, or the like, on an outer surface.

In addition, the leg fixing belt, which allows the leg fixing part to surround and fix the leg according to a thickness of the leg, includes a fastening unit including a Velcro tape, a snap button, a button and a button hole, a buckle, or a combination thereof.

Meanwhile, the varus/valgus correcting device according to the present disclosure may include a correction angle adjusting part 145 adjusting a horizontal angle of the ankle inward or outward. To this end, the present disclosure may adjust and fix the horizontal angle of the corrective shoe 130 and adjust a correction angle of the corrective shoe to reversely rotate the user's tibia and fibula in a normal direction from a bent direction. That is, according to the present disclosure, the correction shoe of the varus/valgus correcting device of the present disclosure may correct varus and valgus by adjusting the correction angle of the corrective shoe according to horizontal rotation.

The correction angle adjusting part may be installed on the corrective shoe support part 140 or on the support frame 112 coupled to the corrective shoe support part 140, and a correction angle of the corrective shoe may be adjusted by adjusting a horizontal angle of the corrective shoe support part 140.

FIG. 3 illustrates the corrective shoe 130 and the correction angle adjusting part 145 of the varus/valgus correcting device 100 according to an embodiment of the present disclosure. As illustrated in FIG. 3, the corrective shoe 130 is connected to a lower portion of the support frame 110 and, specifically, to the lower portion of the lower support frame 112 so that the connection portion of the support frame 110 connected to the corrective shoe 130 is located between the bottom of the corrective shoe 130 and the highest level of the corrective shoe 130. Here, the corrective shoe is configured in the form of a shoe so that the user may fix his or her foot therein. The correction angle adjusting part may be installed at the corrective shoe support part positioned on the rear of the corrective shoe or on the support frame coupled to the corrective shoe support part so that the entire corrective shoe may be horizontally rotated inward or outward on the basis of the correction angle adjusting part as an axis.

Although the correction angle adjusting part is illustrated as a bolt in FIG. 3, but the present disclosure is not limited thereto. The correction angle adjusting part may include any of general fixing devices capable of fixing the lower support frame 112 and the corrective shoe support part 140.

Meanwhile, in order to allow the user to check and adjust a correction angle of the corrective shoe according to a correction stage, the varus/valgus correcting device of the present disclosure may additionally include the correction angle display part 150 displaying a correction angle of the corrective shoe.

Figure 7:
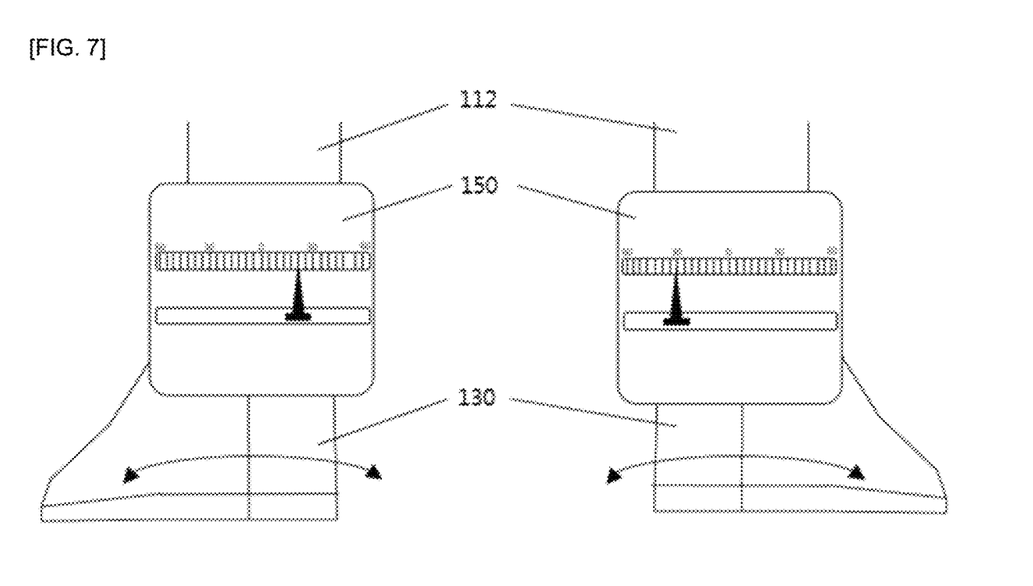
FIG. 7 is a view illustrating a correction angle display part of a varus/valgus correcting device according to an embodiment of the present disclosure.

FIG. 7 is a view illustrating the correction angle display part 150 of the varus/valgus correcting device 100 according to an embodiment of the present disclosure. The correction angle display part 150 may be configured to display a horizontal rotation angle of the corrective shoe support part 140. When the corrective shoe 130 is in a forward direction, the corrective shoe support part 140 is also aligned in the forward direction, and here, the correction angle display part 150 may display a correction angle as 0° and may display both a left side rotation angle and a right side rotation angle.

Meanwhile, the varus/valgus symptoms due to rotation deformity of tibia and fibula are accompanied by rotation deformity of the femur. In order to improve the correction effect, the femur needs to be corrected together with correction of the tibia and fibula, and thus, the varus/valgus correcting device 100 of the present disclosure may include a function of rotationally correcting the femur in an inward direction or outward direction of the leg.

Figure 8:
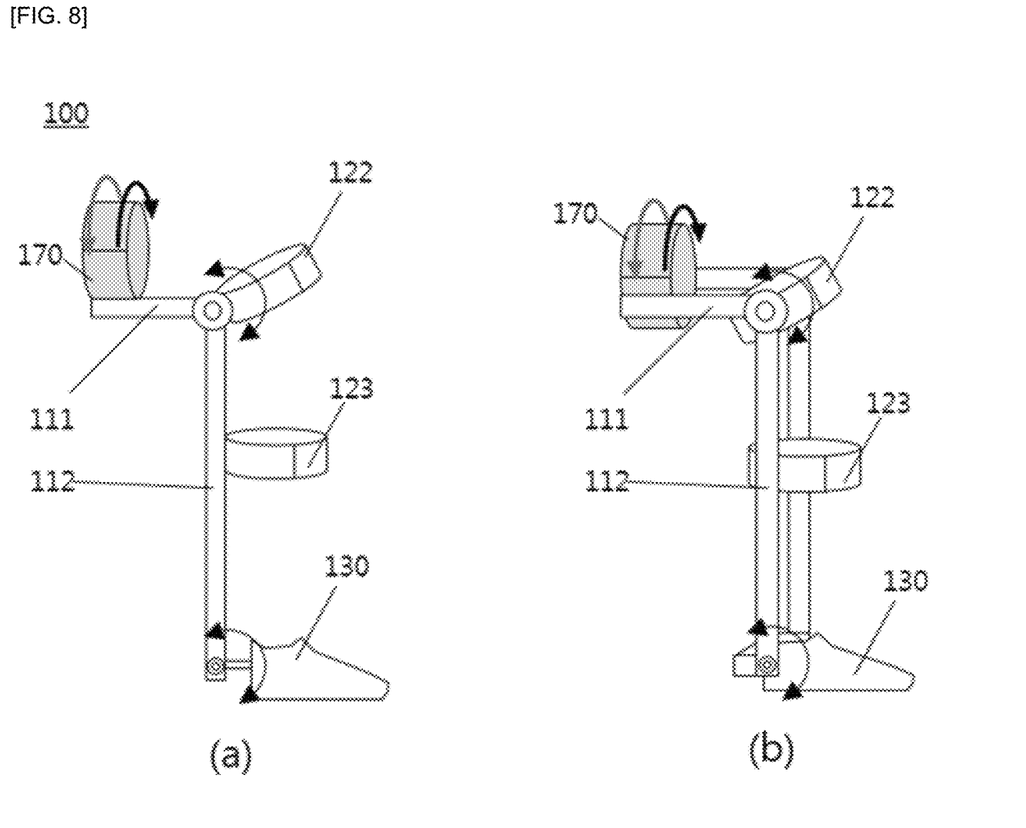

FIG. 8 is a view illustrating a femur correcting part 170 of the varus/valgus correcting device 100 according to an embodiment of the present disclosure. As illustrated in FIG. 8, the varus/valgus correcting device 100 of the present disclosure may include the femur correcting part 170.

For reference, FIG. 8 illustrates the varus/valgus correcting device 100 including the knee fixing part 122 and the calf fixing part 123, as the leg fixing part 120, for example, for the purposes of description.

The femur correcting part 170 according to the present disclosure is connected to the support frame 110. The femur correcting part 170 may surround and fix the upper limb of the leg and rotate in an inward direction or outward direction of the leg to correct the femur in the inward direction or outward direction of the leg.

Specifically, the femur correcting part 170 is connected to the upper support frame 111. The femur correcting part 170 may surround and fix a thigh part of the upper limb of the leg and rotate in the inward direction or outward direction by an angle desired by the user, thus increasing the effect of correction.

That is, when the thigh part of the upper limb of the leg is rotated in the inward direction or the outward direction by the femur correcting part 170, the femur located inside the upper limb of the leg also rotates in the same direction in terms of the body structure, whereby the effect of correction based on the rotation of the femur may be additionally obtained.

The femur correcting part 170 may be formed separately from the femoral fixing part or the femoral fixing part may additionally have a function of rotating in an inward or outward direction of the leg to additionally serve as the femur correcting part.

Also, a rotation direction and a rotation angle of the femur correcting part 170 may be adjusted independently of the corrective shoe, whereby correction may be performed by adjusting the rotational direction and angle of the femur and the tibia and fibula in a customized manner according to varus/valgus symptoms.

To this end, the femur correcting part 170, in a state of being connected to the upper support frame 111, is adjusted to be rotated in one direction (or inward or outward direction of the leg) at a predetermined angle, and after the femur correcting part 170 is completely adjusted, the femur correcting part 170 is fixed to the upper support frame 111 so as not to be rotated any further and the current rotated state of the femur by the femur correcting part 170 is maintained.

In addition, the varus/valgus correcting device 100 of the present disclosure may further include a femur rotation angle adjusting part (not shown) capable of adjusting a rotation angle of the femur in an inward or outward direction of the leg. That is, according to the present disclosure, a rotation angle of the femur may be adjusted and fixed through the femur rotation angle adjusting part, whereby varus/valgus due to rotation deformity of the femur may be corrected by reversely rotating the rotation-deformed femur of the user in a normal direction. The rotation angle adjusting part may be installed on the femur correcting part 170 or on the upper support frame 111 coupled to the femur correcting part 170.

The present disclosure has been described with reference to the accompanying drawings. The embodiments described in the present disclosure and the configurations illustrated in the drawings are merely examples and it will be appreciated that the present disclosure includes all changes, equivalents, or replacements included in the spirit and technical range of the present disclosure as can be understood by a person skilled in the art. Therefore, the technical coverage of the present disclosure should be defined by the appended claims.

The varus/valgus correcting device according to the present disclosure is advantageous in that the knee and ankle may be independently bent or stretched to facilitate movement and the user may stably step on the floor when moving, and since movability is applied to the knee and the ankle joints, the effect of correction may be further maximized so as to be widely applied to the technical field of the varus/valgus correcting device.

What is claimed is:

1. A varus/valgus correcting device comprising:
a support frame supporting at least one of upper and lower limbs of a leg, and formed in a vertical length direction of the leg;
a leg fixing part selected from among a femoral fixing part connected to the support frame and installed to surround and fix the upper limb of the leg, a knee fixing part connected to the support frame and installed to fix a knee part, and a calf fixing part connected to the support frame and installed to surround and fix the lower limb of the leg; and
a corrective shoe connected to a lower portion of the support frame and installed to fix a foot,
wherein
the corrective shoe is horizontally rotated to be adjusted in correction angle to correct varus/valgus,
a connection portion of the support frame connected to the corrective shoe is positioned between a bottom of the corrective shoe and a highest level of the corrective shoe,
a corrective shoe support part connected to a rear side of the corrective shoe, wherein the corrective shoe supporting part connects the corrective shoe to the support frame in a horizontal direction, is provided between the support frame and the corrective shoe, and is positioned between the bottom of the corrective shoe and the highest level of the corrective shoe,
the corrective shoe support part includes a correction angle adjusting part, wherein the correction angle adjusting part is configured to adjust a horizontal angle of the corrective shoe support part such that the corrective shoe rotates around the correction angle adjustment part, the corrective shoe support part further includes an ankle bending part, wherein the ankle bending part is configured such that the corrective shoe rotates around the ankle bending part according to a vertical movement of an ankle, and the corrective shoe support part, the correction angle adjusting part, and the ankle bending part are aligned horizontally.

2. The varus/valgus correcting device of claim 1, wherein the connection portion of the support frame connected to the corrective shoe is positioned on a rear side, a lateral side, or a combination thereof of the corrective shoe.

3. The varus/valgus correcting device of claim 1, wherein the support frame includes an upper support frame supporting an upper limb of the leg; and a lower support frame supporting a lower limb of the leg, and a knee bending part is provided on the upper support frame, the lower support frame, of a coupling portion thereof and has a structure bent according to a bending angle of a knee.

4. The varus/valgus correcting device of claim 3, wherein the upper support frame or the lower support frame each are provided as a single shaft on the rear of the leg or may be provided as a pair of shafts inside or outside the leg.

5. The varus/valgus correcting device of claim 3, wherein the knee bending part is maintained in a straightened state when an external force is not applied by an elastic member including at least one selected from among a spring, a wire, and rubber.

6. The varus/valgus correcting device of claim 1, wherein the correction angle adjusting part includes a correction angle display part displaying a correction angle of the corrective shoe.

7. The varus/valgus correcting device of claim 1, wherein the femoral fixing part and the calf fixing part, when installed at the support frame, are adjustable in height in a length direction of the leg, or the support frame is adjustable in length in a vertical length direction of the leg.

8. The varus/valgus correcting device of claim 1, wherein the leg fixing part includes:

a leg horizontal support part supporting the side of the leg such that the leg is not rotated together according to a change in correction angle of the shoe; and a leg fixing belt allowing the leg horizontal support part to surround and fix the leg according to a thickness of the leg.

9. The varus/valgus correcting device of claim 1, further comprising:

a femur correcting part connected to the support frame, surrounding and fixing the upper limb of the leg, and rotating in an inward direction or outward direction of the leg to correct a femur in the inward direction or outward direction of the leg.

10. The varus/valgus correcting device of claim 9, wherein the leg fixing part is a femoral fixing part and the varus/valgus correcting device allows the femoral fixing part, when installed at the support frame, to include a function of rotating in the inward direction or outward direction of the leg to additionally serve as the femur correcting part.

* * * * *